United States Patent
Wu et al.

(10) Patent No.: US 7,037,711 B2
(45) Date of Patent: May 2, 2006

(54) **PROCESS FOR PRODUCING A CULTURE OF *ANTRODIA CAMPHORATA* AND PRODUCT OBTAINED THEREBY**

(75) Inventors: Mei-Chiao Wu, Hsin-Chu (TW); Ren-Chang Huang, Hua-Lian Hsien (TW); Shie-Jea Lin, Hsin-Chu (TW); Bor-Cheh Wang, Hsin-Chu (TW)

(73) Assignee: Council of Agriculture, Taipei (TW)

( * ) Notice: Subject to any disclaimer, the term of this patent is extended or adjusted under 35 U.S.C. 154(b) by 163 days.

(21) Appl. No.: 10/697,782

(22) Filed: Oct. 30, 2003

(65) Prior Publication Data

US 2004/0091999 A1 May 13, 2004

Related U.S. Application Data

(60) Division of application No. 10/113,903, filed on Mar. 29, 2002, now Pat. No. 6,767,543, which is a continuation-in-part of application No. 09/566,834, filed on May 8, 2000, now Pat. No. 6,391,615.

(30) Foreign Application Priority Data

Feb. 17, 2000 (TW) .............................. 89102716 A

(51) Int. Cl.
*C12N 1/14* (2006.01)
*A01K 65/00* (2006.01)

(52) U.S. Cl. ................ 435/256.8; 435/171; 435/254.1; 435/911; 47/1.1; 424/195.15

(58) Field of Classification Search ................ 435/171, 435/254.1, 911, 195.15, 256.8; 47/1.1; 424/195.15, 424/93.5
See application file for complete search history.

(56) References Cited

U.S. PATENT DOCUMENTS 6,767,543 B1 * 7/2004 Wu et al. .............. 424/195.15

OTHER PUBLICATIONS

Sheng-Hua Wu et al. "*Antrodia camphorate*, new combination of a medicinal fungus in Taiwan". Botanical Bulletin of Academia Sinica (Taipei), 38(4):273-275. ISSN 0006-8063.

* cited by examiner

*Primary Examiner*—Herbert J. Lilling
(74) *Attorney, Agent, or Firm*—Fish & Richardson P.C.

(57) ABSTRACT

The present invention relates to the establishment of a cultivation condition that is suitable for the large-scale production of pharmacologically active filtrates from a culture of *A. camphorata*, in particular, by optimizing the agitation rate and/or pH value during the cultivation. The present invention also relates to a process for obtaining pharmacologically active compositions from a culture of *A. camphorata* through a series of fractionation. This invention is further directed to the uses of the above compositions in the preparation of pharmaceutical compositions.

8 Claims, 6 Drawing Sheets

US 7,037,711 B2

PROCESS FOR PRODUCING A CULTURE OF ANTRODIA CAMPHORATA AND PRODUCT OBTAINED THEREBY

RELATED APPLICATIONS

This application is a divisional application of U.S. application Ser. No. 10/113,903, filed Mar. 29, 2002, now issued as U.S. Pat. No. 6,767,543, which is a continuation-in-part of U.S. application Ser. No. 09/566,834, filed May 8, 2000 now U.S. Pat. No. 6,391,615, which is the country equivalent of Taiwan application Ser. No. 89102716, filed Feb. 17, 2000, disclosure of which is incorporate herein by reference.

FIELD OF THE INVENTION

The present invention relates to the establishment of a cultivation condition that is suitable for the large-scale production of pharmacologically active filtrates from a culture of A. camphorata, in particular, by optimizing the agitation rate and/or pH value during the cultivation. The present invention also relates to a process for obtaining pharmacologically active compositions from a culture of A. camphorata through a series of fractionation. This invention is further directed to the uses of the above compositions in the preparation of pharmaceutical compositions.

DESCRIPTION OF THE RELATED ART

A. camphorata [(Zang & Su) S.-H. Wu, Ryvarden & T. T. Chang], also known as "niu-chang-chih" or "niu-chang-ku" in Taiwan, was recently reported as a new fungus species characterized by the cylindrical shape of its basidiospores appearing in fruit bodies, weakly amyloid skeletal hypha, bitter taste and light cinnamon resupinate to pileate basidiocarps, as well as chlamydospores and arthroconidia in pure culture. The detail characterization and taxonomic position of A. camphorata were described in Chang, T. T. et al., A. cinnamomea sp. nov. on Cinnamomum kanehiral in Taiwan, Mycol. Res. 99(6); 756–758 (1995) and Wu, S.-H., at al., A. cinnamomea ("niu-chang-chih"), New combination of a medicinal fungus in Taiwan, Bot. Bull. Acad. Sin. 38: 273–275 (1997), the entire disclosure of which is incorporated herein by reference.

In Taiwan folk medicine, A. camphorata is believed to have certain medical effects on conditions caused by poisoning, diarrhea, abdominal pain, hypertension, skin itches and liver cancer. However, because of the stringent host specificity and rarity in nature, as well as the failure of artificial cultivation, "niu-chang-chin" is very expensive in local market. Undoubtedly, there exists a great industrial value in developing a cost-effective process for artificial cultivation of this fungus on a large scale.

Recently, the inventors have found that A. camphorata, when subjected to submerged fermentation, exhibits desired pharmacological activity, in particular an anti-tumor activity. As disclosed in U.S. Ser. No. 09/566,834, A. camphorata were successfully cultivated on a small scale in a natural medium, namely potato dextrose broth (PDB), and a synthetic medium containing fructose as the major carbon source. The resultant cultures expressed a color appearance of deep dark red with a redness index $a \geq 3$ as measured using Hunter's coordinate system, which has been shown to coincide with a significant inhibitory effect on the growth of certain tumor cell lines. More importantly, the active substances functioning to the tumor cells, though not identified, were found secreted from the fungal mycelium into the liquid phase of the culture, so that a pharmacologically active composition can be easily harvested from the culture for industrial use.

Accordingly, it would be desirable if such an advantageous process is optimized for large-scale production of the fungal culture. More preferably, the crude filtrate is further fractionated over a desired pharmacological activity so as to obtain useful compositions enriched with the desired activity.

SUMMARY OF THE INVENTION

An extensive investigation has been conducted to fulfill the industrial requirements as indicated above. It has now been unexpectedly found that an optimal condition for the industrial-scale cultivation of A. camphorata can be accomplished by carefully setting certain parameters within particular ranges. In this invention, pH value and agitation speed are found to be critical during cultivation.

Accordingly, the first aspect of the present invention is to provide a process for producing an Antrodia camphorata culture having pharmacological activity, comprising;

(a) inoculating a mycelial inoculum of an isolate of Antrodia camphorata into a medium suitable for growth of said isolate to result in a first culture;

(b) subjecting the first culture cultivated from step (a) to a first stage of agitation which is set at a first predetermined rate and for a first period of time to allow further growth of the inoculated isolate, so as to obtain a second culture proliferation with mycelium; and (c) subjecting the second culture obtained from step (b) to a second stage of agitation which is set at a second predetermined rate different from the first predetermined rate, so as to subject the isolate under physiological stress.

According to the second aspect of the present invention, it is to provide a process for producing an Antrodia camphorata culture having pharmacological activity, comprising:

(a) inoculating a mycelial inoculum of an isolate of Antrodia camphorata into a medium suitable for growth of said isolate; and (b) cultivating the culture resulting from step (a) by adjusting the pH value of the culture to a range from 4.5 to 5.4 throughout step (b).

Preferably, the pH value of the A. camphorata culture is adjusted within a range of 4.6 to 5.3, and more preferably 4.7 to 5.2, throughout the step (b).

The present invention also provides a process for obtaining a series of liquid fractions, which are separated from a culture of A. camphorata over a desired pharmacological activity, such as an anti-tumor activity. Therefore, the third aspect of the present invention is to provide a process for obtaining a pharmacologically active composition from a culture of A. camphorata, comprising:

(a) inoculating a mycelial inoculum of an isolate of A. camphorata into a medium suitable for growth of said isolate;

(b) cultivating the culture resulting from step (a);

(c) removing a major portion of insoluble substances from the culture, whereby a pharmacologically active solution is harvested; and (d) processing the solution from step (c) so as to obtain a pharmacologically active composition containing fungal molecules having a molecular weight of no more than about 10 kDa.

Preferably, the obtained composition contains fungal molecules having a molecular weight of no more than about 3 kDa, more preferably of no more than about 1 kDa.

The fourth aspect of the present invention is to provide a process for obtaining a pharmacologically active composition from a culture of *A. camphorata*, comprising:

(a) Inoculating a mycelial inoculum of an isolate of *A. camphorata* into a medium suitable for growth of said isolate;

(b) cultivating the culture resulting from step (a);

(c) removing a major portion of insoluble substances from the culture, whereby an aqueous solution is harvested;

(d) processing the aqueous solution from step (c) so as to obtain a fraction containing fungal molecules having molecular weights of no more than about 1 kDa; and (e) passing the fraction from step (d) through a water-immiscible phase from which the pharmacologically active composition is obtained.

The water-immiscible phase in the above step (e) is preferably a stationary phase containing an effective amount of an absorbent capable of selectively adsorbing hydrophobic fungal molecules. The stationary phase is eluted so that the pharmacologically active fraction is obtained.

In a preferred embodiment of the invention, the eluate from step (e) is further subjected to reverse-phase partition chromatography, such as on a Lichrosorb® RP-18 column (Merck), to obtain a number of fractions with pharmacological activity.

The present invention further provides pharmaceutical compositions for the treatment of cancer or tumor diseases, which contains a product obtained from any one of the processes according to the present invention.

The present invention further provides a method for the treatment of cancer or tumor diseases in patients in need of such treatment by prescribing the patients with a composition containing a product obtained from any one of the processes according to the present invention.

BRIEF DESCRIPTION OF THE DRAWINGS

The above and other objects and features of the present invention will become apparent with reference to the following description of the preferred embodiment taken in conjunction with the accompanying drawings, in which.

DETAIL DESCRIPTION OF THE INVENTION

Figure 1:
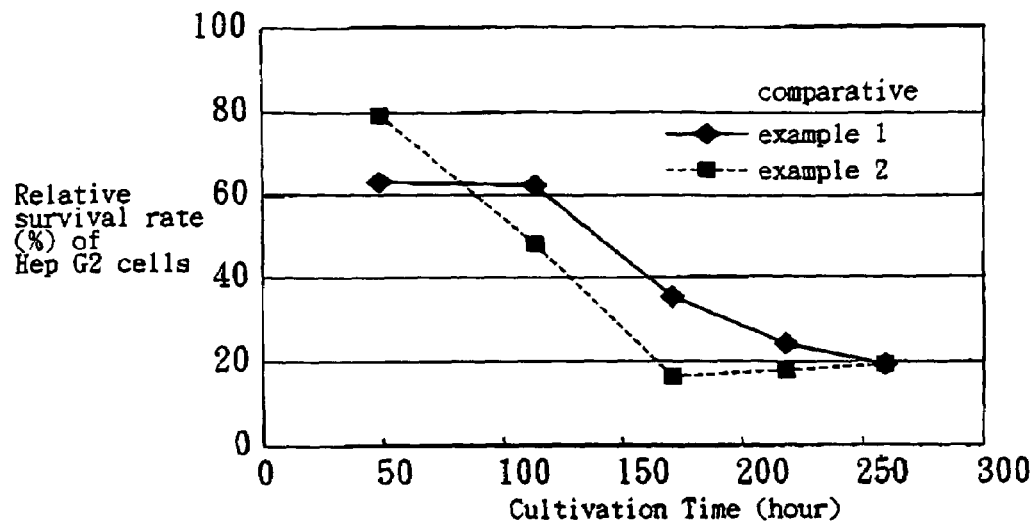
FIG. 1 is a diagram demonstrating the anti-tumor activity of the filtrates derived from *A. camphorata* cultures, where *A. camphorata* is cultivated under two different agitation conditions.
Figure 2:
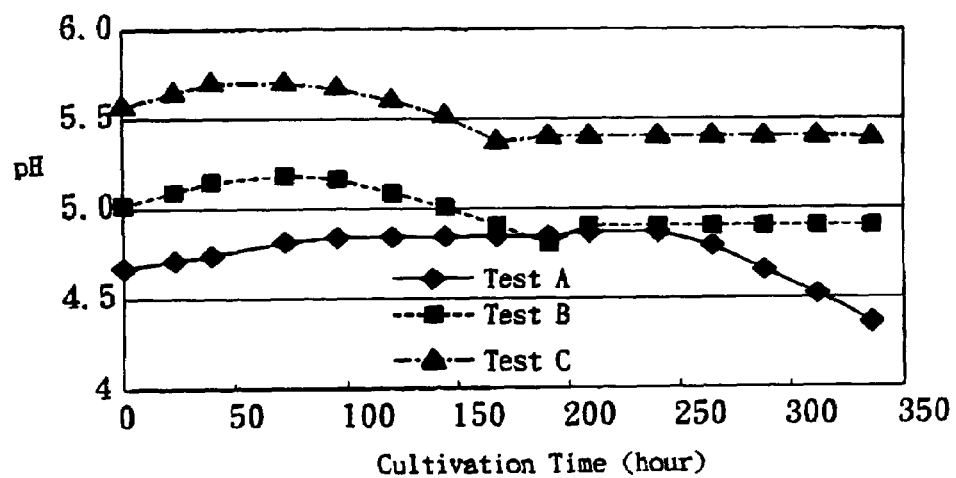
FIG. 2 is a diagram demonstrating the pH fluctuation in three *A. camphorata* cultures over the cultivation time.
Figure 3:
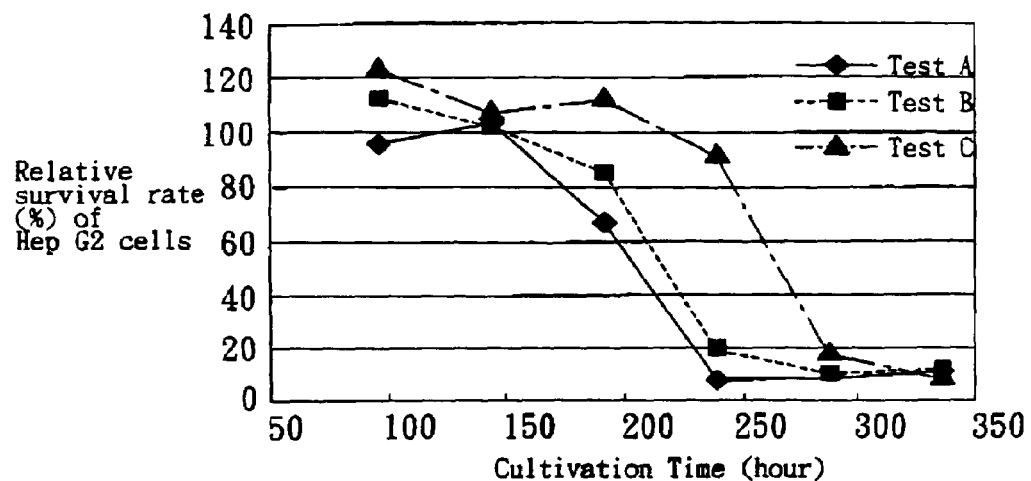
FIG. 3 is a diagram demonstrating the anti-tumor activity of the filtrates derived from the *A. camphorata* cultures described in FIG. 2, where the *A. camphorata* is cultivated at pH values controlled within three distinct intervals.

The present invention generally relates to the establishment of a cultivation condition that is suitable for large-scale production of the pharmacologically active fractions from an *A. camphorata* culture. In accordance with the present invention, the fungus *A. camphorata* is cultivated in a suitable liquid medium to maintain its nutritious growth in mycelial state and facilitate the pharmacological activity thereof.

The term "suitable medium" as used herein is directed to any medium that provides an artificial environment suitable for the growth of *A. camphorata*, while maintaining the pharmacological activity thereof. Preferably, the medium used in the invention is suitable for facilitating the production of the pharmacologically active substance(s) in the mycelium and promoting the secretion thereof into the environment.

The media suitable for used in the present invention include a natural medium named "potato dextrose broth," and any synthetic medium including fructose as the major carbon source. Potato dextrose broth can be prepared in laboratory by, for example, autoclaving an admixture of 300.0 g of diced potato, 20.0 g of dextrose and 1.0 L of distilled water, or purchased from commercial sources, such as DIFCO. The most preferred is the synthetic medium including fructose as the major carbon source. If necessary, other carbon source, such as glucose, sucrose, galactose, fructose, corn starch, malt extract and combinations thereof, can be included in the synthetic medium as an aid. Preferably, the carbon source is present in the range between 1.5–2.5% by weight, and more preferably in an amount of 1.5–2% by weight, on the basis of the total volume of the synthetic medium.

In addition to the carbon source, the synthetic medium may comprise a nitrogen source, trace elements such as an inorganic salt, and optionally vitamins or other growth factors. The nitrogen source includes but is not limited to ammonium sulfate, ammonium nitrate, sodium nitrate, casamino acid, yeast extract, peptone, tryptone, and combinations thereof. Preferably, according to the present invention, the synthetic medium contains yeast extract as the nitrogen source. The nitrogen source is preferably present in the range between 0.2–2.0% by weight, and more preferably in an amount of 0.5% by weight, on the basis of the total volume of the synthetic medium.

Any available isolate of *A. camphorata* can be used in the cultivating process according to the invention, as long as the microorganism used bears the ability to produce a detectable amount of pharmacologically active metabolites. The useful isolates of *A. camphorata* include but are not limited to CCRC 35396 (deposited on Dec. 1, 1994 in the Culture Collection and Research Center (CCRC) of the Food Industry Research and Development Institute (FIRDI), Hsinchu, Taiwan, R.O.C.), 35398 (Dec. 1, 1994), 35716 (May 3, 2000), 36401 (Jan. 27, 2000), 36795 (Jan. 27, 2000) and 930032 (Jan. 27, 2000). According to a preferred embodiment of the invention, *A. camphorata* CCRC 930032, which is also deposited in American Type Culture Center (ATCC)

with an accession number PTA-1233 for the purpose of patent procedure, was employed for the preparation of culture filtrates.

To evaluate the competence in inhibiting the growth of tumor cells, crude filtrates of *A. camphorata* and fractions thereof were subjected to MTT colorimetric assays.

The term "MTT colorimetric assay," also known as "MTT-tetrazolium assay" as used herein, is directed to an anticancer drug screening scheme established in the 1980s by the U.S. National Cancer Institute's Developmental Therapeutics Program, Division of Cancer Treatment (see, for example, Alley, M. C., et al., Feasibility of drug screening with panels of human tumor cell lines using a microculture tetrazolium assay. *Cancer Res.* 48: 589–601, 1988: Scudiero, D. A., et al., Evaluation of a soluble tetrazolium/formazan assay for cell growth and drug sensitivity in culture using human and other tumor cell lines. *Cancer Res.* 48: 4827–4833, 1988; Vistica, D. T., et al., Tetrazolium-based assays for cellular viability: a critical examination of selected parameters affecting formazan. *Cancer Res.* 51: 2515–2520, 1991; and Monks, A., et al., Feasibility of a high-flux anticancer drug screen using a diverse panel of cultured human tumor cell lines. *J. Nat. Cancer Inst.* 83: 757–766, 1991).

In the assay, potential anticancer drugs or natural products derived from plants or microbes (in this case, from *A. camphorata*) were tested for their ability against groups of cell line panels each representing a major clinical category of human malignancy. The viable cell numbers per well are directly proportional to the production of formazan, which can be measured spectrophotometrically through solubilization. In principle, biologically active substances or natural products containing the substances can inhibit or even stop cell growth, and little formazan is formed consequently.

Using the MTT colorimetric assay, the parameters critical in fungal cultivation, i.e., the agitation rate and pH value, are evaluated for their effects on the pharmacological activity of *A. camphorata* over the cultivation time.

In the first set of experiments, an *A. camphorata* culture is duplicated to respectively experience two different courses of agitation, wherein one course is conducted to give a constant but vigorous agitation to the fungus, whereas the other concerns a two-stage agitation from gentle to vigorous. Upon comparison, the two-stage agitation according to the invention results in an early generation of pharmacological activity. The gentle agitation at the former stage is provided to allow the nutritious growth of the inoculated fungus, so that a culture proliferated mycelium can be obtained. The increased sizes of mycelial pellets harvested at the end of cultivation are indicative of success at the gentle agitation stage. The adequate timing for transition of the agitation rate from gentle to vigorous can be varied over a wide range depending upon the fungus isolates chosen. Normally, when a fungal isolate is inoculated at 10% v/v based on the final volume of the culture, the gentle agitation lasted for about 3 days (or about 72 hours) and the agitation rate is elevated afterwards. The vigorous agitation at the later stage is provided to place the fungus under physiological stress. Under such a stress, *A. camphorata* is forced to undergo a plurality of physiological changes in response, including facilitating the production of secondary metabolites that are not expressed in a constitutive manner. It is believed that some fungal molecules of pharmacological activity can be "stressed out" by this way. Other cultivation parameters applicable for giving physiological stress to *A. camphorata*, such as aeration rate, nutrient modification and thermal stress, can also be used alone or in combination with the parameter of agitation rate according to the invention. Suitable agitation rates can be determined empirically as described above, or estimated according to the formula described in, for example, *Bioprocess Engineering Principles*, edited by Pauline M. Doran, published by Academic Press Ltd. (1995), p.150–151, based on the experimental data provided below. In some cases, when the two-stage agitation is applied properly, the fungal cultures appear to turn red on day 6.

In a preferred embodiment of the present invention, the two-stage agitation is carried out in a 5 L fermentor (B. Braun) preloaded with 3 L of medium, wherein the agitation was initially set at a rate of no more than about 300 rpm, preferably about 200 rpm, and subsequently elevated to a rate of no less than about 400 rpm, preferably about 500 rpm. In another preferred embodiment of the invention, the two-stage agitation is carried out in a 250 L fermentor (Bio-Top) preloaded with 160 L of medium, wherein the agitation rate was initially set at about 40 rpm and subsequently elevated to about 150 rpm.

In the second set of experiments, an *A. camphorata* culture is triplicated and respectively cultivated at pH values adjusted within three distinct intervals throughout the entire period of cultivation. Upon comparison, the cultivation conducted at pH 4.5 to 5.4 is found to result in an early generation of pharmacological activity. Preferably, the pH value of the *A. camphorata* culture is adjusted within a range of 4.6 to 5.3, and more preferably 4.7 to 5.2, throughout the entire period of cultivation.

Taking advantage of the useful parameters concerning agitation and pH value as described above, the cultivation process of *A. camphorata* according to the invention is successfully scaled up to 160 liters by volume, while maintaining the desired pharmacological activity derived from the fungus.

According to the process of this invention, a pharmacologically active filtrate from *A. camphorata* available for various industrial applications can be obtained in an economic, efficient and time-saving manner.

The present invention also relates to the establishment of a workable purification process, by which novel compositions of matter enriched with pharmacologically active substances are available for a variety of medical uses. In accordance with the invention, the purification process is conducted by selectively separating a crude filtrate of *A. camphorata* to obtain a fraction containing fungal molecules having molecular weights of no more than about 10 kDa, preferably about 3 kDa, and more preferably about 1 kDa. The separation process can be carried out by any conventional method capable of separating molecules based on molecular weight (i.e., acting as a molecular sieve), examples of which include gel filtration, density gradient purification, ultrafiltration, ultracentrifugation and other like methods known in the art.

According to the invention, the fraction containing molecules with molecular weights of no more than about 1 kDa is further fractionated on the basis of polarity, so as to obtain a water-immiscible phase, from which the pharmacologically active fraction is obtained. The water-immiscible phase can be an insoluble solid phase or an organic phase immiscible with water. In a preferred embodiment of the invention, the $\leq 1$ kDa fraction is passed through a stationary phase containing an effective amount of an absorbent capable of selectively adsorbing hydrophobic fungal molecules. Subsequently, the stationary phase is eluted to obtain a fraction with a desired pharmacological activity. In short, the stationary phase selectively takes up and concentrates hydrophobic solutes, presumably containing the desired pharmacologically active substances, from the ≦1 kDa fraction, so that inactive substances present in the flow through can be readily removed. Suitable absorbent included in the stationary phase can be any absorbent provided with a functional group adapted to capture hydrophobic substances from a mobile phase. Examples of the absorbent are Amberlite® XAD-4 (Sigma) and equivalents thereof. The fractionation can be effectuated by any conventional way, such as incubating the ≦1 kDa fraction with a batch of absorbent, or flowing the ≦1 kDa fraction over a chromatography column packed with the absorbent, as long as the amount of pharmacologically active substances retained on the surfaces of the absorbent is satisfactory. Suitable eluents for eluting the bound substances from the stationary phase are well known in the art and therefore can be readily chosen by those skilled in the relevant field. Preferably, the eluent is an organic solvent having a polarity lower than water and more preferably having a polarity lower than methanol. The most preferred eluents include ethyl acetate and ethanol.

The eluate, which exhibits the desired pharmacological activity, can be subjected to additional purification procedures based on some other physical, chemical or biological characteristics. In a preferred embodiment of the invention, the eluate is further separated based on the degree of hydrobobicty, and more preferably the separation is performed, for example, on a Lichrosorb® RP-18 column (Merck) and the like. A number of fractions so obtained are found to be pharmacologically active.

The above findings strongly suggest that the pharmacological activity in *A. camphorata* is mainly derived from hydrophobic compounds with molecular weights of no more than 1 kDa. This is contrary to a previous hypothesis, in which polysaccarides having an average molecular weight of 500–2,000 kDa are regarded as the main source of anti-tumor activity born by mushrooms (Mizuno, et al., Antitumor-active substances from mushrooms. *Food Rev. Intl.* 11(1); 23–61). While *A. camphorata* is reported to b abundant with low molecular weight substances (Chang, supra; Cherng, et al., Triterpenoids from *Antrodia cinnamomea*. *Pytochem.* 41(1): 263–267 (1996); Chiang, et al., A sesquiterpene lactone, phenyl and biphenyl compounds from *Antrodia cinnamomea*. *Pytochem.* 39(1): 613–616 (1995); and Yang, et. al., Steroids and Triterpenoids of *Antrodia cinnamomea*—a fungus parasitic on *Cinnamomum Micranthum*. *Pytochem.* 41(5): 1389–1392 (1996)), such as triterpenoids, flavinoids, steroids, sesquiterpene lactones, as well as phenyl and biphenyl compounds, no teachings have been reported to bridge these substances and the pharmacological activity of the fungal species.

The purification process according to the invention provides a number of compositions in which active substances are concentrated and inactive substances are extensively removed. The compositions apparently have an enhanced pharmacological effectiveness to a human or animal subject, and are therefore suitable for a variety of industrial applications, such as for the manufacture of a pharmaceutical composition or a nutrient supplement. Therefore, the present invention also relates to the uses of the novel compositions as a medicament for treating disorders, in particular cancer or tumor diseases, in a human or animal patient in need of such treatment, or as a nutrient supplement formulated in the form of, for example, food, beverage and/or animal feed.

Preferred Embodiments for Practicing the Invention

The following Examples are given for the purpose of illustration only and are not intended to limit the scope of the present invention.

EXAMPLE 1

Preparation of Liquid Cultures of *A. camphorata*

Stock culture of *A. camphorata* CCRC 930032 was maintained at −80° C., from which a small aliquot of fungus was picked up and placed on plates of potato dextrose agar (PDA, purchased from DIFCO). After retrieving, the culture was then transferred to slant tubes of potato dextrose agar. The slant cultures were incubated at 25° C. and sub-cultured every two months. The slant cultures were used as working cultures. For the preparation of mycelium inoculum, the PDA plates were inoculated with culture from PDA slants and incubated at 28° C. from 15 to 20 days.

Preparation of Mycelial Inoculum

An incubation was performed until the mycelial colony having a diameter of 15–30 mm is observed. The mycelial characteristics of *A. camphorata* were then investigated under a light microscope to ensure that no contamination occurred. The whole mycelia was cut into small pieces and then homogenized aseptically with 50 ml of sterile water in a homogenizer (Osterizer) for 30 seconds. Aliquots of mycelial suspension were used as inoculum for submerged shake cultures. The inoculum was added in a ratio of 1:9 by volume to a synthetic media (2% of fructose, 0.5% (w/v) of yeast extract (DIFCO), 0.1% (w/v) of $KH_2PO_4$ (Merck), and 0.05% (w/v) of $MgSO_4.7H_2O$ (Merck)) preloaded in Erlenmeyer flasks. The submerged cultures were incubated at 30° C. for 5 days with constant agitation (at 50 rpm on an orbital rotary shaker purchased from Hotech). The resultant cultures were used as inoculum for subsequent large-scale cultivation.

EXAMPLE 2

Effect of Agitation Rate on the Pharmacological Activity of Fungal Filtrates

The inoculum of *A. camphorata* CCRC 930032 prepared in Example 1 was added in a ratio of 1:9 by volume to 2.7 liters of a synthetic media (2% of fructose, 0.5% (w/v) of yeast extract (DIFCO BRL), 0.1% (w/v) of $KH_2PO_4$ (Merck), and 0.05% (w/v) of $MgSO_4.7H_2O$ (Merck)) preloaded in a 5 L fermentor (B. Braun). The culture was incubated at 30° C. with an aeration rate of 0.6 L/min. The agitation rate for the culture was initially set at about 200 rpm and elevated to about 500 rpm after a 74-hour incubation. Specimens were sampled from the culture at the $48^{th}$, $113^{rd}$, $170^{th}$, $217^{th}$ and $259^{th}$ hours after the mycelial inoculation and then passed through a simple filtration assembly of a suction filter funnel, a flask and a vacuum machine to remove a major portion of insoluble substances. The filtrates so harvested were adjusted to pH 7 by $NH_4OH$ and sterilized by autoclaving. The resultant samples were preserved at 4° C. for the subsequent MTT colorimetric assay.

Non-inoculated media were used as a negative control for MTT assay.

Hep G2 tumor cell line was chosen for MTT colorimetric assay. Preparatory to the assay, the cells were maintained as a stock in α-MEM medium (GIBCO BRL), just as ATCC medium, supplemented with 10% fetal bovine serum (Hyclone). The tumor cell line was passaged once or twice weekly using trypsin-EDTA (GIBCO BRL) to detach the cells from cell culture flasks. Tumor cells were harvested, counted and inoculated into a 96-well microtiter plate at a concentration of 3,000 cells per well. The total volume of the cell culture medium in each well was made up to 180 μl, and incubation was carried out overnight at 37° C. in an incubator aerated with 5% $CO_2$.

20 μl aliquots of the samples were applied to the culture wells in triplicate, and the resultant cultures were incubated for 72 hours in the above-mentioned incubation condition. Subsequently, 20 μl of MTT stock solution (Merck), prepared previously at 5 mg/ml in PBS solution (GIBCO BRL) were added to each well.

After an additional 4-hour incubation at 37° C. in a $CO_2$ incubator, the supernatant was removed from each well, and 100 μl of 100% DMSO (dimethyl sulfoxide, available from Sigma) were added, in order to solubilize the MTT-formazan product. After thorough mixing with a mechanical plate mixer, absorbance at 540 nm was measured with an ELISA reader (MRX, Dynex). The relative survival rates of tumor cells in the tested filtrates were calculated by dividing the absorbance of each experimental sample by that of the corresponding non-inoculated control.

COMPARATIVE EXAMPLE 1

Example 2 was repeated except that the fungal culture was incubated at a constant rate of about 500 rpm throughout the entire period of cultivation.

The relative survival rates of tumor cells after the treatment of the filtrates from Example 2 and Comparative Example 1 are compared in Table 1 and FIG. 1.

TABLE 1

| Sampling Time | Relative survival rate (%) of Hep G2 cells | |
|---|---|---|
| (hour) | Comparative Example 1 | Example 2 |
| 48 | 63 | 79 |
| 113 | 62 | 48 |
| 170 | 35 | 16 |
| 217 | 24 | 18 |
| 259 | 19 | 19 |

In Table 1, filtrates sampled at the indicated time points are compared for the inhibitory effect on Hep G2 tumor cells. For the filtrates picked up at the $170^{th}$ hour after the mycelial inoculation, it can been seen that A. camphorata CCRC 930032, when experienced a two-stage agitation from 200 rpm to 500 rpm, gives a relative survival rate of 16% in the MTT assay, which is much more effective than the culture cultivated at a constant rate of 500 rpm from which a higher relative survival rate of 35% is observed. The anti-tumor activities of Example 2 and Comparative Example 1 got closer at later time points (at the $217^{th}$ and $259^{th}$ hours), suggesting that an initial agitation at lower rate in combination with a higher agitation rate at the later stage would accomplish an early production of the pharmacologically active substance(s) in culture media.

Consistent results were observed in the counterpart experiments using AGS, HeLa and MCF-7 tumor cell lines in the MTT assay (data not shown).

EXAMPLE 3

Effect of pH Value on the Pharmacological Activity of Fungal Filtrates

Three batches of synthetic media (1.5% of fructose, 0.5% (w/v) of yeast extract (DIFCO BRL), 0.1% (w/v) of $KH_2PO_4$ (Merck), and 0.05% (w/v) of $MgSO_4.7H_2O$ (Merck)) were prepared to have initial pH values of about 4.5 (Test A), 5.0 (Test B) and 5.5 (Test C), respectively, to which the inoculum prepared in Example 1 was added in a ratio of 1:9. The resultant cultures were cultivated as described in Example 2, except that the pH value of each culture was monitored at predetermined time points and carefully adjusted around the initial pH value by addition of a NaOH solution (Table 2). The cultivation lasted for 336 hours. The timing for the addition of NaOH solution varied depending on the pH value chosen. For instance, Test B and Test C were added with aliquots of NaOH solution since the $192^{nd}$ and $168^{th}$ hours to maintain the pH value between about 4.9–5.1 and about 5.4–5.6, respectively, whereas NaOH solution was not added into Test A until the $240^{th}$ hour.

TABLE 2

| Sampling Time | pH | | |
|---|---|---|---|
| (hour) | Test A | Test B | Test C |
| 0 | 4.67 | 5.02 | 5.58 |
| 24 | 4.71 | 5.05 | 5.65 |
| 40 | 4.74 | 5.09 | 5.7 |
| 72 | 4.81 | 5.15 | 5.71 |
| 96 | 4.84 | 5.16 | 5.68 |
| 120 | 4.84 | 5.09 | 5.61 |
| 144 | 4.84 | 5.01 | 5.52 |
| 168 | 4.84 | 4.9 | 5.37 |
| 192 | 4.85 | 4.81 | 5.4 |
| 209 | 4.86 | 4.9 | 5.4 |
| 240 | 4.86 | 4.9 | 5.4 |
| 264 | 4.8 | 4.9 | 5.4 |
| 288 | 4.66 | 4.9 | 5.4 |
| 312 | 4.52 | 4.9 | 5.4 |
| 336 | 4.37 | 4.9 | 5.39 |

Specimens sampled from the culture at the $96^{th}$, $144^{th}$, $192^{nd}$, $240^{th}$, $288^{th}$ and $366^{th}$ hours after the mycelial inoculation and then passed through a simple filtration assembly of a suction filter funnel, a flask and a vacuum machine to remove a major portion of insoluble substances. The filtrates so harvested were adjusted to pH 7 by $NH_4OH$ and sterilized by autoclaving. The resultant samples were subjected to an MTT colorimetric assay as shown in Example 2. Non-inoculated media were used as a negative control for MTT assay.

TABLE 3

| Sampling Time | Relative survival rate (%) of Hep G2 cells | | |
|---|---|---|---|
| (hour) | Test A | Test B | Test C |
| 96 | 96 | 112 | 123 |
| 144 | 103 | 102 | 107 |
| 192 | 67 | 85 | 112 |
| 240 | 8 | 19 | 91 |
| 288 | 9 | 10 | 18 |
| 336 | 11 | 12 | 8 |

As shown in Table 3, the *A. camphorata* filtrates sampled at the indicated time points are compared for the inhibitory effect on Hep G2 tumor cells. For the filtrates picked up at the $192^{nd}$ hour after the mycelial inoculation, it can be seen that the *A. camphorata* CCRC 930032 cultivated in Test A and Test B yields relative survival rates lower than that observed in Test C. Such differences in antitumor effects come to maximum at the $240^{th}$ hour and gradually decrease at later time points, suggesting that a cultivation conducted at pH 4.5 to 5.4, preferably at 4.6 to 5.3, and more preferably at 4.7 to 5.2, would accomplish an early production of the pharmacologically active substance(s) in culture media.

Consistent results were observed in the counterpart experiments using AGS, HeLa and MCF-7 tumor cell lines in the MTT assay (data not shown).

EXAMPLE 4

Scaled-Up Cultivation of *A. camphorata* in a 250 L Fermentor

The inoculum of *A. camphorata* CCRC 930032 prepared in Example 1 was added in a ratio of 1:9 by volume to 160 liters of a synthetic media (1.5% of fructose, 0.5% (w/v) of yeast extract (DIFCO BRL), 0.1% (w/v) of $KH_2PO_4$ (Merck), and 0.05% (w/v) of $MgSO_4.7H_2O$ (Merck)) preloaded in a 250 L fermentor (Bio-Top). The culture was incubated at 30° C. with an aeration rate of 0.6 L/min. The agitation rate for the culture was initially set at about 40 rpm and elevated to about 150 rpm after a 70-hour incubation. The pH value of the culture was adjusted within a range of 4.9 to 5.1 throughout the entire period of cultivation.

Specimens were sampled from the culture at the $96^{th}$, $144^{rd}$, $168^{th}$, $186.5^{th}$, $244^{th}$ and $284^{th}$ hours after the mycelial inoculation and then filtrated by a conventional method to remove a major portion of insoluble substances. The filtrates so harvested were adjusted to pH 7 by $NH_4OH$ and sterilized by autoclaving. The resultant samples were subjected to an MTT colorimetric assay, in which HeLa, AGS, Hep G2 and MCF-7 cells were tested at a start-up concentration of 1,000, 3,000, 3,000 and 3,000 cells per well. Non-inoculated media were used as a negative control for MTT assay. The results are shown in Table 4 and FIG. 4.

TABLE 4

| Sampling Time | Relative survival rate (%) of the tested cells | | | |
|---|---|---|---|---|
| (hour) | HeLa | AGS | Hep G2 | MCF-7 |
| 96 | 89 | 83 | 91 | 61 |
| 144 | 70 | 67 | 49 | 38 |
| 168 | 65 | 32 | 36 | 31 |
| 186.5 | 30 | 26 | 33 | 22 |
| 244 | 23 | 34 | 42 | 26 |
| 284 | 25 | 37 | 43 | 26 |

Figure 4:
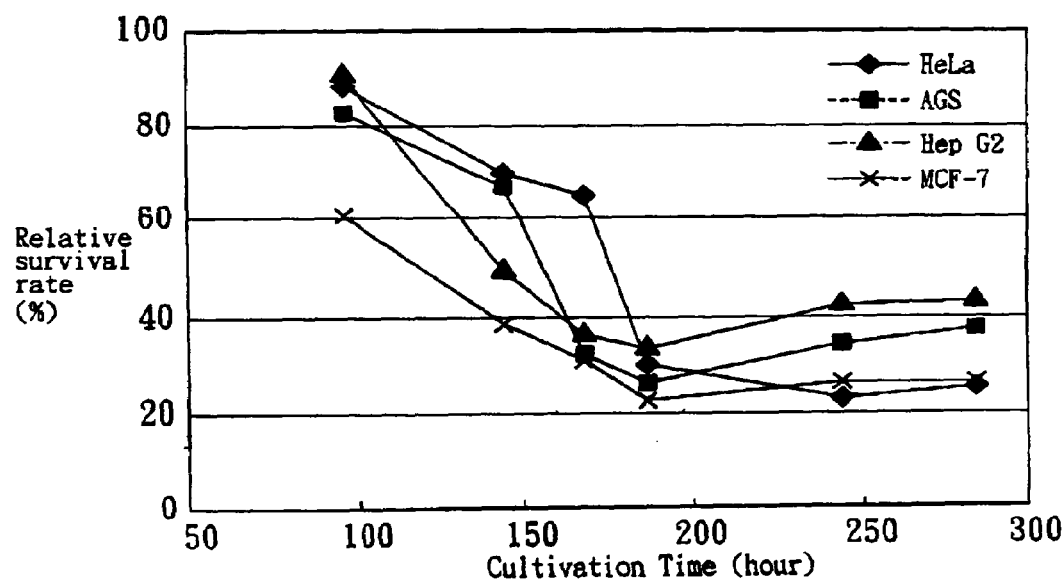
FIG. 4 is a diagram demonstrating the anti-tumor activity of the filtrates derived from a scaled-up culture of *A. camphorata;*

Table 4 and FIG. 4 show that the cultivation process of *A. camphorata* according to the invention is successfully scaled up to 160 liters by volume, through setting the agitation rate and pH value within the desired ranges described in Examples 2 and 3.

EXAMPLE 5

Preparation of a Culture Filtrate of *A. camphorata* in Synthetic Media

Whole mycelia of *A. camphorata* CCRC 930032 cultivated on a PDA plate was cut into small pieces and then homogenized aseptically with 50 ml of sterile water in a homogenizer (Osterizer) for 30 seconds, so that a mycelial suspension was obtained. To 200 ml of a synthetic media (2% of fructose, 0.5% (w/v) of yeast extract (DIFCO), 0.1% (w/v) of $KH_2PO_4$ (Merck), and 0.05% (w/v) of $MgSO_4.7H_2O$ (Merck)) preloaded in 1 L Erlenmeyer flasks, 20 ml of the mycelial suspension was added. The submerged culture was incubated at 30° C. for 14 days with constant agitation (at 75 rpm on an orbital rotary shaker purchased from Hotech). At the end of incubation, the fungus culture was passed through a simple filtration assembly of a suction filter funnel, a flask and a vacuum machine. The crude filtrate was used for the subsequent analysis.

EXAMPLE 6

Preparation and Analysis of Active Fractions from *A. camphorata* Filtrate

The crude filtrate from Example 5 (F0) was passed through a Certriprep® Concentrator 10 (a commercial mini-column purchased from Amicon which having a molecular weight cut-off value of 10 kDa) by centrifugation at low speed, according to the protocol provided by the manufacturer. The primary flow-through solution is named fraction F1. The column was then refilled with deionized water and the centrifugation was repeated to collect a secondary flow-through F2. The fungal molecules retained in the column were harvested and referred to as F3.

Figure 5:
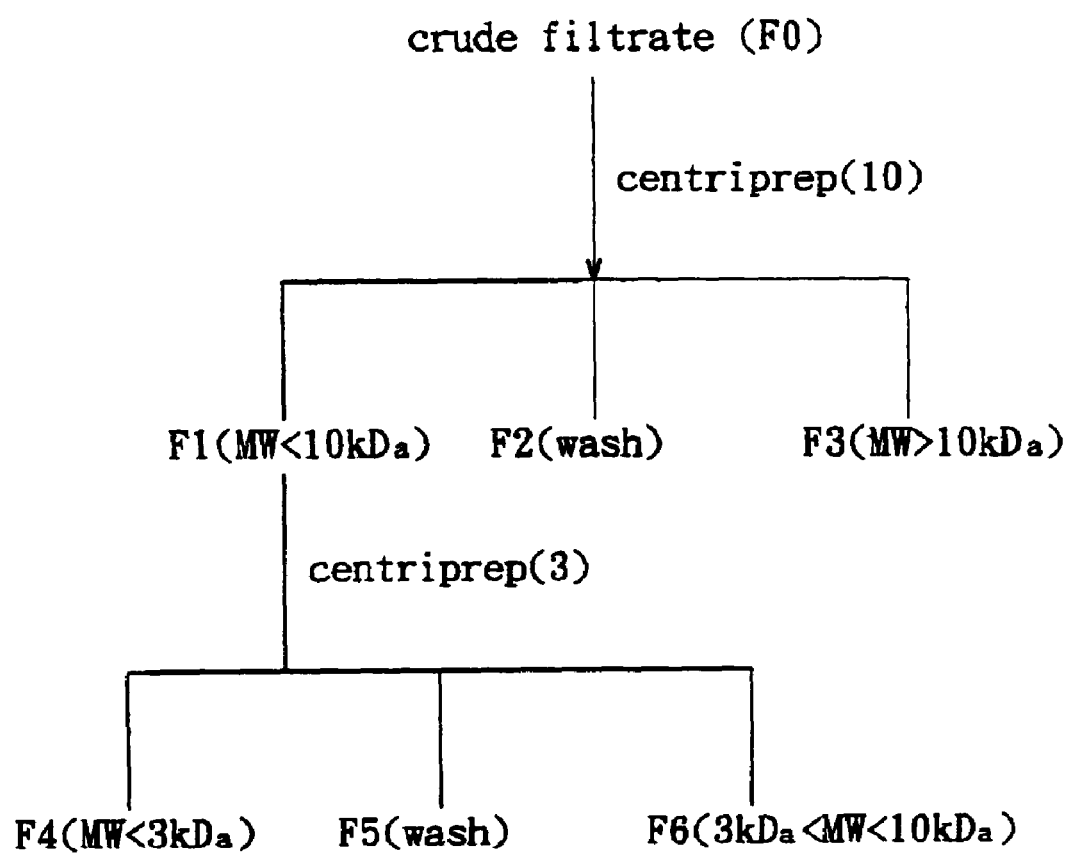
FIG. 5 is a flow chart illustrating the purification scheme for an *A. camphorata* filtrate based on molecular weight.

F1 was further fractionated by a Certriprep® Concentrator 3 mini-column (Amicon) which has a molecular weight cut-off value of 3 kDa, so that a primary flow-through (F4), a secondary flow-through (F5) and a fraction retained in the mini-column (F6) were obtained as described above. The purification scheme is shown in FIG. 5.

Figure 6:
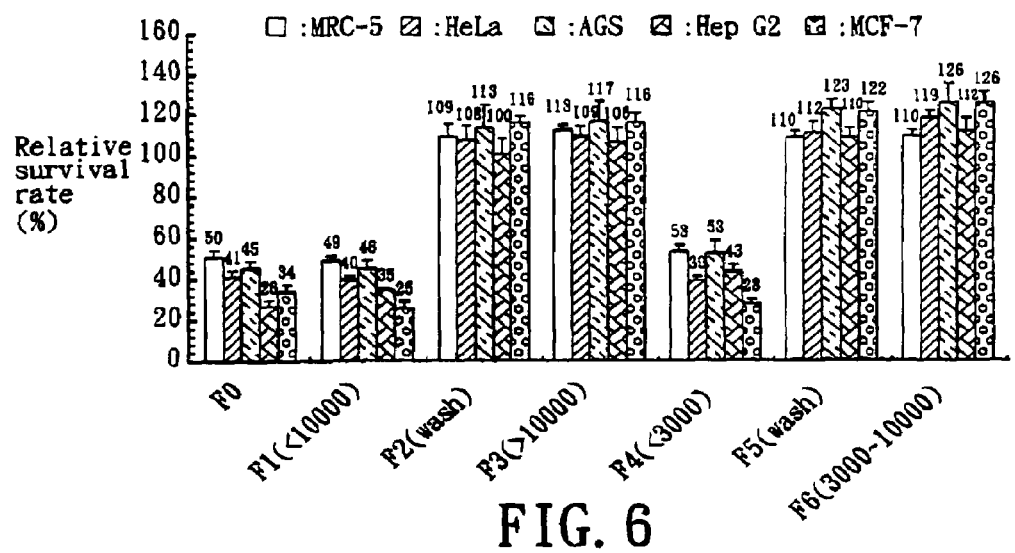
FIG. 6 is a bar graph demonstrating the anti-tumor activity of the culture filtrates separated according to FIG. 5, in which the tested cell lines include MRC-5, HeLa, AGS, Hep G2, and MCF-7.

The resultant fractions were subjected to an MTT colorimetric assay to evaluate the competence in inhibiting the growth of tumor cells. In this case, HeLa cells were tested at a start-up concentration of 1500 cells per well, whereas MRC-5, AGS, Hep G2 and MCF-7 cells were initially loaded to have 3,000 cells per well. As clearly demonstrated in FIG. 6, the anti-tumor activities exhibited by both F1 and F4 are comparable to that of the crude filtrate (F0). The result suggests that most of the pharmacologically active substances present in the filtrate, if not all, are of low molecular weights, in particular of a molecular weight of no more than about 3 kDa.

The crude filtrate from Example 5 (F0) was also fractionated through a series of membrane filters, so as to obtain a fraction containing fungal molecules having molecular weights of no more than 1 kDa (F7). The fact that the anti-tumor activity is co-fractionated with F7 (FIG. 7, the leftmost panel) indicates that the apparent molecular weights of the pharmacologically active substances could be down to no more than about 1 kDa.

In the MTT assay described above, a reduced survival rate was observed in the filtrate-treated MRC-5 cells (normal lung fibroblast cells), indicating that the fungal filtrate and its active fraction may exhibit certain suppressive effects on normal cells. However, when MRC-5 cells were inoculated up to, for example, 10,000 cells per wells, the suppressive effect will decrease dramatically. As a comparison, the effectiveness of the fungal filtrate and its active fraction were much less affected by an increased amount of tumor cells (data not shown). This in vitro observation leads to a presumption that the compositions according to the invention, when administered into a living subject, are pharmacologically friendly to normal tissues but would inflict a severe impact on tumor at the same time.

EXAMPLE 7

Separation of *A. camphorata* Filtrate on Amberlite® XAD-4 Resins

The Fraction F7 from Example 6 was incubated with a batch of Amberlite® XAD-4 (Sigma) with gentle stirring. After completion of the incubation, the resin beads were precipitated by centrifugation. The supernatant containing unadsorbed substances and the resin beads were harvested separately. Afterwards, the beads were sequentially eluted with equal volumes of deionized water, methanol and ethyl acetate, and the eluates from the three courses of elution were collected separately. The methanol eluate and ethyl acetate eluate were evaporated to dryness under reduced pressure and redissolved in small amounts of ethanol. The ethanol solutions so obtained were added with appropriate amounts of sterile water, so that the final concentration of ethanol in the follow-up MTT colorimetric assay is adjusted to no more than 0.5%. The MTT colorimetric assay was conducted as described in Example 6 using non-inoculated media or 0.5% ethanol in water as negative control. The results are shown in FIG. 7.

Figure 7:
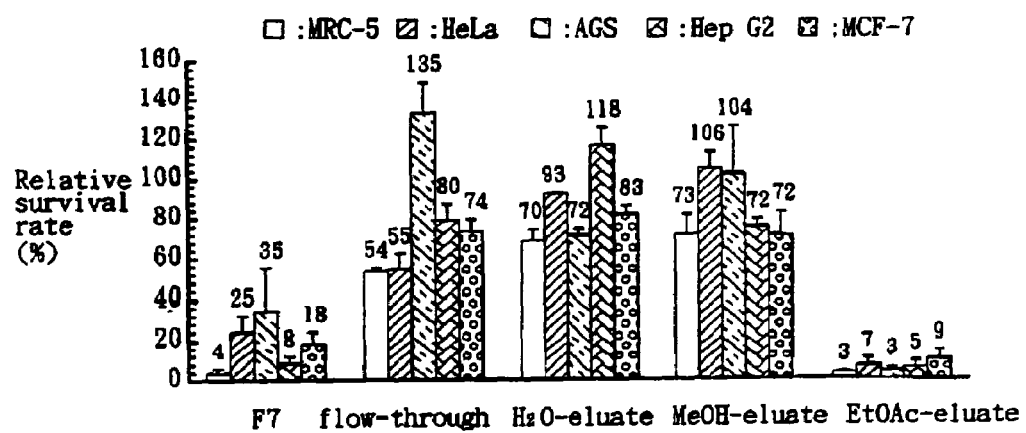
FIG. 7 is a bar graph comparing the anti-tumor activity of the fractions separated on Amberlite® XAD-4 from a filtrate fraction containing fungal molecules having molecular weights of no more than 1 kDa, in which the tested cell lines include MRC-5, HeLa, AGS, Hep G2, and MCF-7.

In FIG. 7, the ethyl acetate eluate is shown to have an excellent anti-tumor activity against all the five types of cells, while the water and methanol eluates do not exhibit a significant effect on the cells. Residual anti-tumor activity was observed in the supernatant portion, which is presumed to result from the incompletion adsorption of hydrophobic substances by the resins. The results suggest that the pharmacological activity present in the filtrate is mainly derived from hydrophobic substances of molecular weights of no more than about 1 kDa.

EXAMPLE 8

Separation of *A. camphorata* Filtrate on a Lichrosorb RP 18 Column

Figure 8:
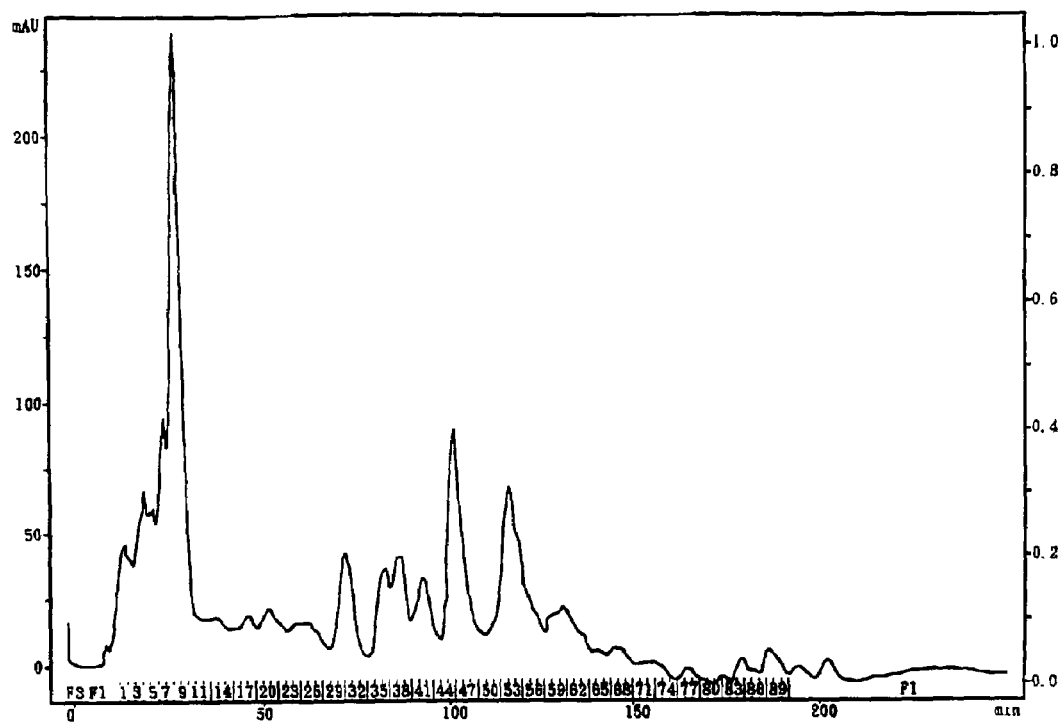
FIG. 8 is a spectrum profile of the ethyl acetate eluate of FIG. 7 fractionated on a Lichrosorb® RP-18 column.

The ethyl acetate eluate from Example 7 was further separated on a Lichrosorb® RP-18 column (Hibar, pre-packed column RT 250-25; 7 μm; purchased from Merck). Gradient elution was performed using an eluent of acetonitrile/water with an acetonitrile percentage from 40% to 100% over 200 minutes at a flow rate of 5.7 ml/min. The absorbance at 254 nm was measured and plotted in FIG. 8. 12-ml fractions were collected and combined into several fractions as shown in Table 5.

TABLE 5

| Fraction | Tube no. |
|---|---|
| A | 1, 2 |
| B | 3, 4, 5 |
| C | 6 |
| C' | 7, 8, 9, 10 |

TABLE 5-continued

| Fraction | Tube no. |
|---|---|
| D | 11, 12, 13, 14 |
| E | 15, 16, 17 |
| F | 18, 19, 20, 21 |
| G | 23, 24, 25, 26 |
| H | 28, 29, 30, 31 |
| I | 33, 34, 35 |
| J | 36, 37, 38 |
| K | 39, 40, 41, 42 |
| L | 43, 44, 45, 46 |
| M | 50, 51, 52, 53 |
| N | 57, 58, 59, 60 |
| P | 69, 70, 71, 72, 73 |
| Q | 74, 75, 76, 77 |
| R | 80, 81 |
| S | 82, 83, 84 |
| T | 85, 86, 87, 88 |

The fractions were evaporated to dryness under reduced pressure and prepared into working solutions as described in Example 7. An MTT colorimetric assay was conducted as described in Example 6. The results are shown in FIGS. 9–11.

Figure 9:
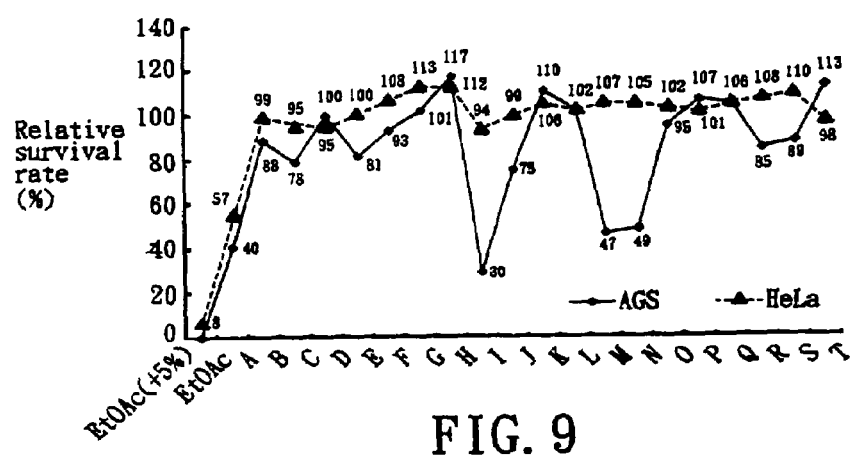
FIGS. 9–11 demonstrate the anti-tumor activity of the fractions separated in FIG. 8.
Figure 10:
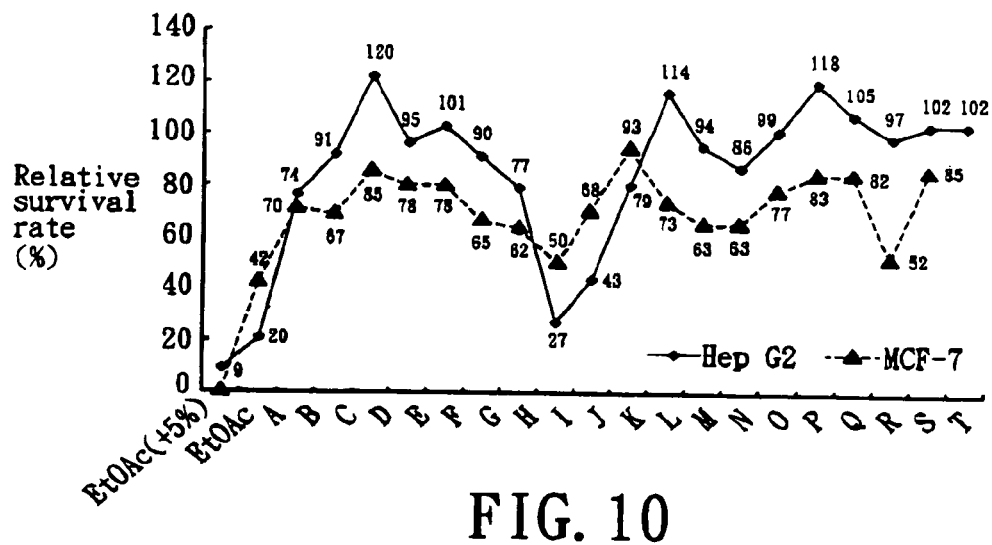
Figure 11:
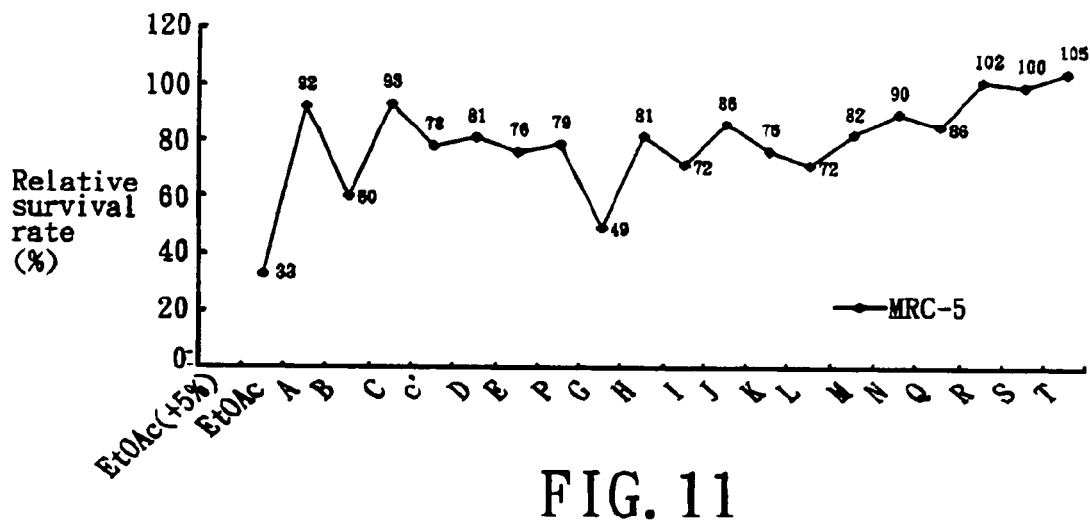

As demonstrated in FIGS. 9–11, fractions G, K and L exhibit a significant inhibitory effect on AGS cells, whereas adjacent fractions G and H suppress the survival rates of Hep G2 cells to a level of lower than 50%. MCF-7 cells have a broad spectrum of being inhibited by fractions B, E, F, G, H, K, L and R. However, the inhibitory activity on HeLa cells found in the ethyl acetate eluate was almost eliminated during the purification on the reverse-phase partition chromatography, indicating that some pharmacological activities in *A. camphorata* filtrate may come from a cooperative action of various molecules and this cooperation is rather vulnerable to vigorous purification.

While the invention has been described with reference to the above specific embodiments, it should be recognized that various modifications and changes, which will be apparent to those skilled in the relevant art, may be made without departing from the spirit and scope of the invention.

We claim:

1. A process for producing an *Antrodia camphorata* culture having pharmacological activity, comprising:
   (a) inoculating a mycelial inoculum of an isolate of *Antrodia camphorata* into a medium suitable for growth of said isolate to result in a first culture;
   (b) subjecting the first culture cultivated from step (a) to a first stage of agitation which is set at a first predetermined rate and for a first period of time to allow further growth of the inoculated isolate, so as to obtain a second culture proliferation with mycelium; and
   (c) subjecting the second culture obtained from step (b) to a second stage of agitation which is set at a second predetermined rate higher than the first predetermined rate, so as to subject the isolate under physiological stress.

2. The process of claim 1, wherein the first culture from step (a) and the second culture from step (b) are cultivated in steps (b) and (c) by adjusting to a pH value ranging from 4.5 to 5.4.

3. The process of claim 2, wherein the first culture from step (a) and the second culture from step (b) are cultivated in steps (b) and (c) by adjusting to a pH value ranging from 4.6 to 5.3.

4. The process of claim 3, wherein the first culture from step (a) and the second culture from step (b) are cultivated in steps (b) and (c) by adjusting to a pH value ranging from 4.7 to 5.2.

5. The process of claim 1, wherein the medium used in step (a) is selected from the group consisting of potato dextrose broth, and a synthetic medium containing fructose as a major carbon source.

6. The process of claim 5, wherein the medium used in step (a) is a synthetic medium containing fructose as a major carbon source.

7. The process of claim 1, wherein the isolate of *Antrodia camphorata* used in step (a) is selected from the group consisting of CCRC 930032 (ATCC PTA-1233), CCRC 35396, 35398, 35716, 36401 and 36795.

8. The process of claim 1, wherein the cultivated culture obtained from step (c) has an inhibitory activity against tumor or cancer cells.

* * * * *

UNITED STATES PATENT AND TRADEMARK OFFICE
CERTIFICATE OF CORRECTION

| | | |
|---|---|---|
| PATENT NO. | : 7,037,711 B2 | Page 1 of 1 |
| APPLICATION NO. | : 10/697782 | |
| DATED | : May 2, 2006 | |
| INVENTOR(S) | : Ren-Chang Huang and Bor-Cheh Wang | |

It is certified that error appears in the above-identified patent and that said Letters Patent is hereby corrected as shown below:

Title Page, Item (75)
    Item [75], INVENTORS,
    Line 1, delete "Mei-Chiao Wu, Hsin-Chu (TW);"
    Line 3, delete "Shie-Jea Lin, Hsin-Chu (TW);"

Signed and Sealed this

Twenty-third Day of January, 2007

JON W. DUDAS
*Director of the United States Patent and Trademark Office*